(12) United States Patent
Wang et al.

(10) Patent No.: US 10,779,974 B2
(45) Date of Patent: Sep. 22, 2020

(54) ABSORBABLE ENDOLUMINAL STENT AND PRODUCTION METHOD THEREOF

(71) Applicants: SHANGHAI BIO-HEART BIOLOGICAL TECHNOLOGY CO., LTD., Pudong District, Shanghai (CN); FU WAI HOSPITAL, CAMS & PUMC, Xicheng District, Beijing (CN)

(72) Inventors: Guohui Wang, Shanghai (CN); Bo Xu, Shanghai (CN); Yongjian Wu, Shanghai (CN)

(73) Assignees: SHANGHAI BIO-HEART BIOLOGICAL TECHNOLOGY CO., LTD., Pudong District, Shanghai (CN); FU WAI HOSPITAL, CAMS & PUMC, Xicheng District, Beijing (CN)

( * ) Notice: Subject to any disclaimer, the term of this patent is extended or adjusted under 35 U.S.C. 154(b) by 0 days.

(21) Appl. No.: 14/960,860

(22) Filed: Dec. 7, 2015

(65) Prior Publication Data

US 2016/0175121 A1      Jun. 23, 2016

(30) Foreign Application Priority Data

Dec. 19, 2014   (CN) .......................... 2014 1 0815199

(51) Int. Cl.
   *A61F 2/915*   (2013.01)
   *A61F 2/91*    (2013.01)
   (Continued)

(52) U.S. Cl.
   CPC ................ *A61F 2/91* (2013.01); *A61F 2/915* (2013.01); *B29C 70/745* (2013.01);
   (Continued)

(58) Field of Classification Search
   CPC ........ A61F 2/82–945; A61F 2/24–2475; A61F 2250/0068; A61F 2002/91558–91566
   See application file for complete search history.

(56) References Cited

U.S. PATENT DOCUMENTS

| 5,603,721 A * | 2/1997 | Lau | A61F 2/88 |
| | | | 604/103.09 |
| 6,709,452 B1 * | 3/2004 | Valimaa | A61F 2/88 |
| | | | 623/1.15 |

(Continued)

FOREIGN PATENT DOCUMENTS

| CN | 102371670 A | 3/2012 |
| CN | 202184823   | 4/2012 |

(Continued)

OTHER PUBLICATIONS

Chinese Office Action for corresponding Chinese Patent Application No. 201410815199.3 dated Feb. 29, 2016, 16 pgs.

*Primary Examiner* — Rebecca S Preston

(74) *Attorney, Agent, or Firm* — Merchant & Gould P.C.

(57) ABSTRACT

An absorbable endoluminal stent and method for preparing the same are provided in the present invention. The absorbable endoluminal stent comprises a stent body, a plurality of through holes formed in the stent body, and bioabsorbable polymeric materials filled in the through holes. When the stent is implanted into the blood vessels, damages on stent caused during crimping and expansion processes are reduced. Radical supporting force duration of stent is (Continued)

improved and mechanical properties of stent after implantation are guaranteed by compositing the materials in the through holes and materials of the stent body.

15 Claims, 2 Drawing Sheets

(51) Int. Cl.
*B29C 70/74* (2006.01)
*B29K 105/00* (2006.01)
*B29L 31/00* (2006.01)
*B29C 49/04* (2006.01)

(52) U.S. Cl.
CPC ............... *A61F 2002/91558* (2013.01); *A61F 2002/91566* (2013.01); *A61F 2002/91575* (2013.01); *A61F 2210/0004* (2013.01); *A61F 2230/0006* (2013.01); *A61F 2230/0008* (2013.01); *A61F 2230/0017* (2013.01); *A61F 2230/0069* (2013.01); *A61F 2240/001* (2013.01); *A61F 2250/003* (2013.01); *A61F 2250/0015* (2013.01); *A61F 2250/0059* (2013.01); *A61F 2250/0068* (2013.01); *B29C 49/04* (2013.01); *B29C 2791/009* (2013.01); *B29K 2105/258* (2013.01); *B29K 2995/006* (2013.01); *B29L 2031/7534* (2013.01); *B29L 2031/7543* (2013.01)

(56) References Cited

U.S. PATENT DOCUMENTS

| | | | | |
|---|---|---|---|---|
| 8,741,378 | B1* | 6/2014 | Roorda | B05D 1/02 |
| | | | | 427/2.24 |
| 2002/0007209 | A1* | 1/2002 | Scheerder | A61F 2/915 |
| | | | | 623/1.15 |
| 2005/0283228 | A1* | 12/2005 | Stanford | A61F 2/91 |
| | | | | 623/1.15 |
| 2010/0274349 | A1* | 10/2010 | Lord | A61F 2/91 |
| | | | | 623/1.16 |
| 2011/0137407 | A1* | 6/2011 | Nguyen | A61F 2/91 |
| | | | | 623/1.42 |
| 2011/0223212 | A1* | 9/2011 | Taton | A61L 27/34 |
| | | | | 424/400 |
| 2011/0245904 | A1* | 10/2011 | Pacetti | A61F 2/91 |
| | | | | 623/1.15 |
| 2012/0158123 | A1* | 6/2012 | Borck | A61L 31/06 |
| | | | | 623/1.15 |
| 2013/0197620 | A1 | 8/2013 | Brown et al. | |
| 2013/0317596 | A1* | 11/2013 | Rapoza | A61F 2/86 |
| | | | | 623/1.16 |

FOREIGN PATENT DOCUMENTS

| | | |
|---|---|---|
| CN | 102740806 A | 10/2012 |
| CN | 103857363 A | 6/2014 |
| CN | 204411039 | 6/2015 |

* cited by examiner

ABSORBABLE ENDOLUMINAL STENT AND PRODUCTION METHOD THEREOF

CROSS-REFERENCE TO RELATED APPLICATION

This application claims a priority to Chinese Patent Application No. 201410815199.3 filed on Dec. 19, 2014, the disclosures of which are incorporated in their entirety by reference herein.

TECHNICAL FIELD

The present disclosure relates to the field of medical devices, in particular to an absorbable endoluminal stent and a method for preparing the same.

BACKGROUND

Since a German doctor Andreas •Grüntzig firstly proposed an idea of stent in 1976, until the coronary stents are widely used in clinical treatment in the 90's in the 20th century, the third-generation of absorbable drug eluting stent has already appeared. However, at present, for the drug-eluting stents (DES) based on stainless steel and cobalt-chromium alloy, a certain percentage of patients still suffer from subacute thrombosis and restenosis problems after implanting the stents. Moreover, such metal stents permanently remain in the body. Therefore, the bioabsorbable vascular stents (BVS) started be focused and highlighted.

The absorbable stent theoretically has many potential benefits: the normal vascular contractility can recover after the stent is absorbed, and the occurrence of restenosis is prevented; vasomotoricity which disappears after the implantation of the ordinary stent is reconstructed; intervention in the same lesioned part can be performed repeatedly; it can be used for children suffering from congenital diseases without frequent re-intervention being needed.

The drug-eluting absorbable stent is the future direction of development, this study and other related tests represent a forefront of the cardiovascular study, however, the duration of radial supporting force providing by the absorbable stents is worth focusing on and needs further study at present. Variation on the duration of radial supporting force is mainly derived from whether there is a damage on the stent due to the materials or the processes before the implantation, and for the existing macromolecular polymer stents, since there are two essential processes of crimping and expansion to go through, the damages occur on the stress concentration areas, which affect the mechanical properties after the implantation. In this regard, in order to reduce the damage caused during the implantation of the stents of polymeric material, Japan's Igaki-Tamai poly-lactic acid stent has been proposed to fill high temperature contrast agent in a balloon for reducing the damage on stent in the expansion process. Another improving method is to heat the stent invivo by an external magnetic field to reduce the damages on the stent in the expansion process. However, these methods all require a step of heating the stent after implantation in the blood vessel. Since the stent is in contact with the blood vessel wall, heating the stent invivo is very likely to cause damage and necrosis of an arterial wall, which is followed by complications of smooth muscle cell proliferation and resulting in the in-stent restenosis.

SUMMARY

The technical problem to be solved is to provide an absorbable endoluminal stent and a method for preparing the same. When the stent is implanted in the blood vessels, damage which occurs during crimping and expansion processes is reduced by the compositing materials in the through holes and the materials of the stent itself.

To solve the above problems, an embodiment of the present invention provide an absorbable endoluminal stent, comprising stent body, a plurality of through holes formed in the stent body, and a bioabsorbable polymeric material filled in the through holes. In the present invention, bioabsorbable polymeric material occasionally is abbreviated as filling material.

In one example, the stent body has a network structure, comprising undulating main-structure struts in multiple columns and connecting struts, each of which connects between the adjacent main-structure struts;

each column of the main-structure struts of the stent body is formed by a plurality of basic-structure struts which is integrally interconnected end-to-end, and the main-structure strut is bilaterally symmetrical relative to connecting struts extension direction; wherein the basic-structure strut comprises: the first V-shaped struts having a crest and two elongated portions extending from the crest of the first V-shaped strut and the second V-shaped struts having a crest and two elongated portions extending from the crest of the second V-shaped strut, which are alternately connected end-to-end, and a plurality of through holes formed in the first V-shaped struts and/or the second V-shaped struts; one end of the connecting strut is integrally connected to a crest of the first V-shaped strut, and another end is integrally connected to a crest of the second V-shaped strut in an adjacent column;

the crest of the first V-shaped struts is an m-shaped crest, and the crest of second V-shaped struts is an n-shaped crest.

In one example, the plurality of through holes are distributed in the crests of the first V-shaped struts, the crests of the second V-shaped struts, as well as troughs formed by integrally connecting the first V-shaped struts and the second V-shaped struts, or distributed in the whole area of the stent body.

In one example, the cross section of the through hole is of a circular, elliptical, polygonal and irregular shape.

In one example, the wall thickness of the stent body is 100~250 micrometers, and the area of the cross section of the through hole is 10~23,000 square microns.

In one example, the stent body is made of a bioabsorbable polymeric material which is same as or different from the filling material.

In one example, the bioabsorbable polymeric material is one or more selected from poly-lactic acid (PLA), L-poly-lactic acid (L-PLA), D-poly lactic acid (D-PLA), poly-DL-lactic acid (PDLLA), poly-caprolactone (PCL), poly-trimethylene carbonate (PTMC), poly-p-dioxanone (PPDO), Poly-orthoester (POE), or, a copolymer or a blend obtained by compounding all or a part of the materials above according to the predetermined properties, and the molecular weight is 30,000~400,000.

In one example, the stent body is made of PLA having a molecular weight of 300,000, and the filling material is PCL having a molecular weight of 50,000~100,000.

To solve the above problems, the present invention also provides a method for preparing an absorbable endoluminal stent, which comprises:

step 1, extruding a bioabsorbable polymeric material to obtain a tube, then conducting thermal expansion of tube by blow molding to obtain a thin-walled tube, and carving the thin-walled tube into a stent body by laser engraving;

step 2, forming a plurality of through holes in areas of the stent body on which a stress is concentrated while being crimped and/or expanded, or whole area of the stent body by laser engraving;

step 3, filling the through holes with bioabsorbable polymeric material.

In one example, the step 3 comprises:

step 3a, configuring the bioabsorbable polymeric material as spherical fillers, and embedding the spherical fillers into the through holes;

step 3b, nesting mold tubes on the inner and outer walls of the stent body, then heating in a vacuum oven at 60° C.~80° C. for 30 minutes~2 hours, until the stent material is tightly combined with the filling material.

In one example, the step 3 comprises:

step 3a', dissolving the bioabsorbable material in a dissolvent to obtain a solution, then injecting the solution into the through holes;

step 3b', nesting mold tubes on the inner and outer walls of the stent body, then drying in a vacuum oven at 30° C.~40° C. for 30 minutes~12 hours;

step 3c'', repeating the above steps 3a'~3b', until the through holes are filled with filling material.

In one example, the step 3 comprises:

step 3a'', putting bioabsorbable polymeric pellets into a heating injector at 60° C.~70° C. until the material therein is in a molten state, then perfusing the material in the molten state into the through holes;

step 3b'', nesting mold tubes on the inner and outer walls of the stent, then heating in a vacuum oven at 60° C.~80° C. for 30 minutes~2 hours, until the stent material is tightly combined with the filling material.

In one example, in the step 2, the through holes are further formed by chemical etching or physical punching.

The above-mentioned technical solutions in the present invention at least include following beneficial effects:

in the above solutions, through holes are formed in area in the stent body on which the stress in concentrated while the stent is crimped or expanded, namely, a plurality of through holes are formed in crests of the first V-shaped struts, crests of the second V-shaped struts, as well as troughs formed by integrally connecting the first V-shaped struts and the second V-shaped struts. Additionally, bioabsorbable polymeric material such as poly-caprolactone (PCL) is used to fill the through holes, and the filling material and the stent material are tightly combined by heating and drying with a vacuum oven. There does not exist a process of heating stent invivo throughout the whole stent implantation process, and only through compositing the materials of through holes and materials of the stent body. Damages during crimping and expansion processes are reduced. Radical supporting force duration is improved, and mechanical properties after implantation are guaranteed.

DESCRIPTION OF MAIN REFERENCE SIGN OF THE DRAWINGS

Figure 1:
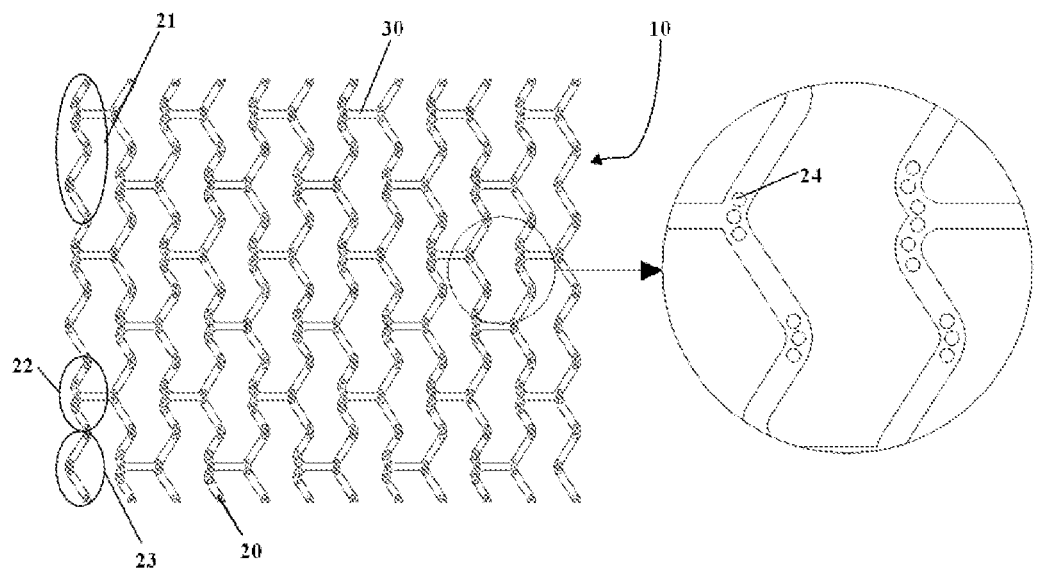
FIG. 1 is a schematic view of a developed surface of the absorbable endoluminal stent in an embodiment of the present invention.

10 Stent body, 20 Main-structure strut, 21 Basic-structure strut, 22 The first V-shaped strut, 23 The second V-shaped strut, 24 Through hole, 30 Connecting strut

DETAILED DESCRIPTION

In order to clarify the technical problems to be solved, technical solutions and advantages of the present invention, embodiments of the present invention are described in conjunction with examples below. These descriptions only illustrate features and advantages of the present invention, and do not limit the scope of protection of the invention.

With reference to disadvantages of prior art, namely, that since there are two essential processes of crimping and expansion for macromolecular polymer stents to go through, the damages occur on the stress concentrated areas, which affect the mechanical properties after the implantation, as well as it is necessary to heat the stent invivo to reduce the damages. The present invention provide an absorbable endoluminal stent and method for preparing the same, wherein through holes are formed in an area in the stent body where a stress is concentrated while the stent is crimped or expanded, namely, through holes are formed in the crests of the first V-shaped struts, the crests of the second V-shaped struts, as well as troughs formed by integrally connecting the first V-shaped struts and the second V-shaped struts, and additionally, the bioabsorbable polymeric material such as poly-caprolactone (PCL) is used to fill through holes, and the filling material and the stent material are tightly combined by heating and drying with a vacuum oven. Therefore, there is no need to heat it invivo during the stent implantation process, and only through compositing the materials of through holes and the materials of stent body, the damages caused during crimping and expansion processes are reduced. Radical supporting force duration is effectively improved, and mechanical properties after stent implantation are guaranteed.

In examples of the present invention, the material of stent body 10 and the filling material preferably have a molecular weight between 40,000~300,000 and include but not limited to one or more materials selected from poly-lactic acid (PLA), L-poly-lactic acid (L-PLA), D-poly lactic acid (D-PLA), poly-DL-lactic acid (PDLLA), poly-caprolactone (PCL), poly-trimethylene carbonate (PTMC), poly-p-dioxanone (PPDO), Poly-orthoester (POE), or, a copolymer or a blend obtained by compounding all/a part of the materials mentioned above according to predetermined properties. For example, the filling material can be the bioabsorbable polymeric material having a molecular weight of 50,000~100,000. The same or different bioabsorbable polymeric materials can be selected and used for stent body 10 and the filling material. All materials used in the absorbable endoluminal stent in examples of the present invention are bioabsorbable polymeric materials, which have good biocompatibility and are gradually decomposed in 3 months after the stent being implanted in the body, and are eventually decomposed into non-toxicity absorbable products for human body such as water and carbon dioxide, and restore the blood vessels to natural state after the stent disappearing.

In example 1 of the present invention, as shown in FIG. 1 which is a schematic view of a developed surface of the absorbable endoluminal stent in an embodiment of the invention. PLA having a molecular weight of 300,000 is selected and extruded to form a tube, and then a thermal expansion is conducted for the tube by blow molding to obtain a thin-wall poly-lactic acid tube having a wall thickness of 100 μm, which is then processed to be a stent body 10 by laser engraving technique. Optionally, slag thereof is removed by adopting physical means to obtain the stent body 10, and subsequently, through holes 24 having the area of the cross-section of 10~23,000 square microns, for example, having the area of the cross-section of 5,000~10,000 square microns, are formed in the stent body 10 by laser engraving technique.

Specifically, the stent body 10 has a network structure, comprising undulating main-structure struts 20 in multiple columns and connecting struts 30, each of which connects between the adjacent main-structure struts 20; each column of the main-structure strut 20 of the stent body is formed by a plurality of basic-structure struts 21 which is integrally interconnected end-to-end, and the main-structure strut 20 is bilaterally symmetrical relative to connecting struts extension direction; wherein the basic-structure strut 21 comprises: the first V-shaped strut 22 having a crest and two elongated portions extending from the crest of the first V-shaped strut 22 and the second V-shaped strut 23 having a crest and two elongated portions extending from the crest of the second V-shaped strut 23, which are alternately connected end-to-end, and a plurality of through holes 24 which are formed in the first V-shaped strut 22 and/or the second V-shaped strut 23; one end of the connecting strut is integrally connected to a crest of the first V-shaped strut 22, and another end is integrally connected to a crest of the second V-shaped strut 23 in an adjacent column; the crest of the first V-shaped strut is an m-shaped crest, and the crest of the second V-shaped strut is an n-shaped crest. The through holes are formed in an area on which a stress is concentrated while the stent is crimped or expanded, namely, are formed in crests of the first V-shaped struts, crests of the second V-shaped struts, as well as troughs formed by integrally connecting the first V-shaped struts and the second V-shaped struts. Apparently, the plurality of through holes 24 also can be formed in the whole area of the stent body 10.

Figure 2:
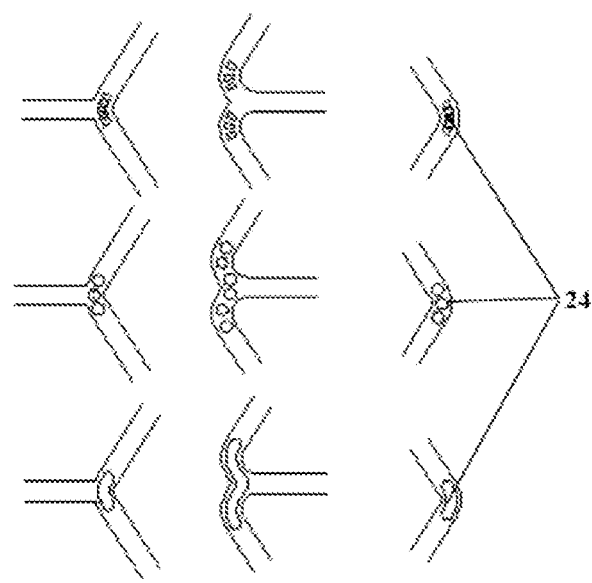
FIG. 2 is a schematic view of several collocation relation of through holes in an embodiment of the present invention.

Wherein, as shown in FIG. 2 which is a schematic view of several kinds of collocation relation of through holes in an embodiment of the present invention, from top to bottom, the cross section of the through holes 24 respectively are polygonal, circular, and irregular shape. It should be noted that the polygonal, circular, irregular shape exemplified above are only examples, not limiting the scope of protection of the present invention. The cross section of the through holes 24 can also be oval, triangular, heart-shaped, star-shaped and so on.

Figure 3:
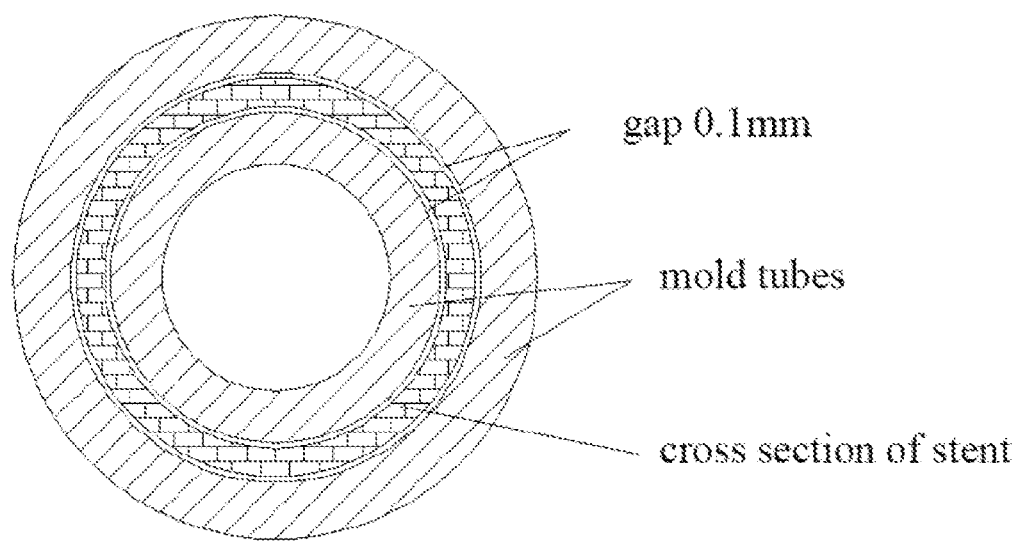
FIG. 3 is a schematic view of mold tubes in an embodiment of the present invention.

PCL material having a molecular weight of 100,000 is configured as spherical material having a diameter of 50~200 μm, and placed in through holes 24 on stent body 10; as shown in FIG. 3 which is a schematic view of mold tubes in an embodiment of the present invention, a 304 stainless mold tube having an outer diameter which is less than inner diameter of the stent by 0.1 mm is nested on the inner surface of the stent, and a 304 stainless mold tube having an inner diameter which larger than the outer diameter of the stent by 0.1 mm is nested on the outer surface of stent; and then the stent is placed in a vacuum oven under protective atmosphere of helium gas at 60° C.~80° C., for example at 62° C., 65° C., 68° C., 70° C., 72° C., 74° C., 76° C., 78° C., and heated for 30 minutes~2 hours, for example for 40 minutes, 60 minutes, 80 minutes, 100 minutes, so that the stent material tightly combine with the filling material. The stent is gradually decomposed in 3 months after being implanted into the human body, and is eventually decomposed into non-toxicity absorbable products for human body such as water and carbon dioxide, and restore the blood vessels to natural state after the stent disappearing.

In example 2 of the present invention, as shown in FIG. 1~3, poly-trimethylene carbonate (PTMC) having a molecular weight of 300,000 is selected and extruded to form a tube, and then a thermal expansion is conducted for the tube by blow molding to obtain a thin-wall poly-lactic acid tube having a wall thickness of 250 μm, which is then processed to be a stent body 10 by laser engraving technique. Optionally, slag thereof is removed by adopting physical means to obtain the stent body 10. Irregular-shaped through holes 24 having the area of the cross-section of 5,000~10,000 square microns are formed in the stent body 10 by physical punching technique; PCL material having a molecular weight of 50,000 is dissolved in the dissolvent at the ratio of 1:5~1:100 to obtain a solution, which is then injected into the through holes 24, then placed and dried in a vacuum oven under protective atmosphere of helium gas at 30° C.~40° C., for example at 32° C., 35° C., 37° C., 39° C., which is repeated for many times until though holes 24 are filled with PCL. The stent is processed in the vacuum oven for 30 minutes~12 hours, for example, for 1 hour, 2 hours, 3 hours, 4 hours, 5 hours, 6 hours, 7 hours, 8 hours, 9 hours, 10 hours, 11 hours. In the above example of the present invention, the dissolvent can be one or more solvent of tetrahydrofuran, chloroform, dichloromethane or acetone. The stent is gradually decomposed in 3 months after being implanted into the human body, and is eventually decomposed into non-toxicity absorbable products for human body such as water and carbon dioxide, and also restore the blood vessels to natural state after stent disappearing.

In example 3 of the present invention, as shown in FIG. 1-3, Poly-orthoester (POE) having a molecular weight of 300,000 is selected and extruded to form a tube, and then a thermal expansion is conducted for the tube by blow molding to obtain a thin-wall tube having a wall thickness of 250 μm, which is then processed to be a stent body 10 by laser engraving technique. Optionally, slag thereof is removed by adopting physical means to obtain the stent body 10. Polygonal through holes 24 having the area of the cross-section of 10,000 square microns, are formed in the stent body 10 by chemical etching technique; PCL material pellet having a molecular weight of 100,000 is put into a heating injector at 60° C.~70° C., for example, at 62° C., 65° C., 68° C. to become in the molten state, and then PCL material in the molten state is extruded into through holes 24; as shown in FIG. 3, a 304 stainless mold tube having an outer diameter which is less than inner diameter of the stent by 0.1 mm is nested on the inner surface of the stent, and a 304 stainless mold tube having an inner diameter which larger than the outer diameter of the stent by 0.1 mm is nested on the outer surface of stent; and subsequently, the stent is placed in a vacuum oven under vacuum atmosphere at 60° C.~80° C., for example, at 62° C., 65° C., 68° C., 70° C., 72° C., 74° C., 76° C., 78° C., and heated for 30 minutes~2 hours, for example, for 40 minutes, 60 minutes, 80 minutes, 100 minutes, so that the stent material tightly combine with the filling material. The stent is gradually decomposed in 3 months after implanted into the human body, and is eventually decomposed into non-toxicity absorbable products for human body such as water and carbon dioxide, and also restore the blood vessels to natural state after stent disappearing.

The absorbable endoluminal stent in the present invention at least include the following advantages: there does not exist the process of heating the stent invivo throughout the whole stent implantation process, and only through compositing materials in through holes and materials of stent body. Damages caused during crimping and expansion processes are reduced. Radical supporting force duration is improved, and mechanical properties after implantation are guaranteed.

The above-mentioned is a preferred embodiment of the present invention, it should be indicated that for those of ordinary skill in the art, on the premise of not departing from the principles of the present invention, some improvements and modifications can be made, and these improvements and modifications also should be considered the scope of protection of the present invention.

What is claimed is:

1. An absorbable endoluminal stent, comprising: a stent body, a plurality of through holes formed in the stent body, and only a bioabsorbable polymeric material filled in the through holes,
wherein the stent body has a network structure and consists of undulating main-structure struts in multiple columns and connecting struts, each of which connects between the adjacent main-structure struts;
wherein each column of the main-structure strut of the stent body is formed by a plurality of basic-structure struts integrally interconnected end-to-end, and the main-structure strut is bilaterally symmetrical relative to a connecting strut extension direction;
wherein each of the basic-structure strut comprises: a first V-shaped strut having a crest and two elongated portions extending from the crest of the first V-shaped strut, and a second V-shaped strut having a crest and two elongated portions extending from the crest of the second V-shaped strut, the first and second V-shaped struts in each column being alternately and integrally connected end-to-end, forming a trough at each integral connection between a first and second V-shaped struts, wherein one end of each of the connecting struts is integrally connected to the crest of one of the first V-shaped struts, and another end of the connecting strut is integrally connected to the crest of one of the second V-shaped strut in an adjacent column;
wherein the crest of each the first V-shaped struts is an m-shaped crest, and the crest of the second V-shaped strut is single-peaked crest;
wherein the plurality of through holes are formed in the crests of the first V-shaped struts, the crests of the second V-shaped struts, as well as in the troughs formed at the integral connections between the first V-shaped struts and the second V-shaped struts; and
wherein a bioabsorbable polymeric material which is made of the stent body is poly-lactic acid (PLA) having a molecular weight of 30,000-400,000, the bioabsorbable polymeric material filled in the through holes is poly-caprolactone (PCL) having a molecular weight of 50,000~100,000, and the poly-lactic acid (PLA) which is made of the stent body and the poly-caprolactone (PCL) filled in the through holes are combined by heating the stent in a vacuum oven at a temperature of 60° C. to 80° C. for a period of time of 30 minutes to 2 hours.

2. The absorbable endoluminal stent according to claim 1, wherein a cross section of each of the plurality of through holes is of a circular shape.

3. The absorbable endoluminal stent according to claim 1, wherein a wall thickness of the stent body is 100~250 micrometers, and an area of the cross section of the through holes is 10~23,000 square microns.

4. The absorbable endoluminal stent according to claim 1, wherein the bioabsorbable polymeric material PLA has a molecular weight of 300,000.

5. The absorbable endoluminal stent according to claim 1, wherein an area of the cross section of the through holes is 5,000~10,000 square microns.

6. The absorbable endoluminal stent according to claim 1, wherein a cross section of the through holes is of elliptical, polygonal and irregular shape.

7. The absorbable endoluminal stent according to claim 1, wherein a cross section of the through holes is of a triangular, heart or star shape.

8. The absorbable endoluminal stent of claim 1, wherein both the elongated portions extending from the crests of the first and second V-shaped struts are substantially without through holes.

9. The absorbable endoluminal stent according to claim 1, wherein the filling bioabsorbable polymeric material PCL is combined with the bioabsorbable polymeric material PLA by heating and drying with the vacuum oven.

10. A method for preparing an absorbable endoluminal stent, comprising:
step 1: extruding a first bioabsorbable polymeric material to obtain a tube, then conducting thermal expansion of tube by blow molding to obtain a thin-walled tube, and carving the thin-walled tube into a stent body by laser engraving;
step 2: forming a plurality of through holes in areas of the stent body on which a stress is concentrated while the stent is crimped and/or expanded, or in the whole area of the stent body by laser engraving; and
step 3: filling the through holes with only a second bioabsorbable polymeric material,
wherein the absorbable endoluminal stent comprising: the stent body, the plurality of through holes formed in the stent body, and only the second bioabsorbable polymeric material filled in the through holes,
wherein the stent body has a network structure and consists of undulating main-structure struts in multiple columns and connecting struts, each of which connects between the adjacent main-structure struts;
wherein each column of the main-structure strut of the stent body is formed by a plurality of basic-structure struts integrally interconnected end-to-end, and the main-structure strut is bilaterally symmetrical relative to a connecting strut extension direction;
wherein each of the basic-structure strut comprises: a first V-shaped strut having a crest and two elongated portions extending from the crest of the first V-shaped strut, and a second V-shaped strut having a crest and two elongated portions extending from the crest of the second V-shaped strut, the first and second V-shaped struts in each column being alternately and integrally connected end-to-end, forming a trough at each integral connection between a first and second V-shaped struts, wherein one end of each of the connecting struts is integrally connected to the crest of one of the first V-shaped struts, and another end of the connecting strut is integrally connected to the crest of one of the second V-shaped strut in an adjacent column;
wherein the crest of each the first V-shaped struts is an m-shaped crest, and the crest of the second V-shaped strut is single-peaked crest;
the areas of the stent body on which a stress is concentrated in which the plurality of through holes are formed are the crests of the first V-shaped struts, the crests of the second V-shaped struts, as well as in the troughs formed at the integral connections between the first V-shaped struts and the second V-shaped struts; and wherein the first bioabsorbable polymeric material which is made of the stent body is poly-lactic acid (PLA) having a molecular weight of 30,000-400,000, the second bioabsorbable polymeric material filled in the through holes is poly-caprolactone (PCL) having a molecular weight of 50,000~100,000, and the poly-lactic acid (PLA) which is made of the stent body and the poly-caprolactone (PCL) filled in the through holes are combined by heating the stent in a vacuum oven at a temperature of 60° C. to 80° C. for a period of time of 30 minutes to 2 hours.

11. The method for preparing an absorbable endoluminal stent according to claim 10, wherein the step 3 comprises:
step 3a: configuring the second bioabsorbable polymeric material filled in the through holes as spherical fillers, and embedding the spherical fillers into the through holes; and
step 3b: nesting mold tubes on inner and outer walls of the stent body, then heating in the vacuum oven at 60° C.~80° C. for 30 minutes~2 hours until the first bioabsorbable polymeric material of the stent body is combined with the second bioabsorbable polymeric material.

12. The method for preparing an absorbable endoluminal stent according to claim 11, wherein in the step 3, after nesting the mold tubes on the inner and outer wall of the stent body, the method further comprises drying in an vacuum oven at 65° C.~76° C. for 40 minutes~100 minutes.

13. The method for preparing an absorbable endoluminal stent according to claim 10, wherein the step 3 comprises:
step 3a": placing pellets of the second bioabsorbable polymeric material in a heating injector at 60° C.~70° C. until the second bioabsorbable polymeric material therein is in a molten state, then perfusing the second bioabsorbable polymeric material in the molten state into the through holes;
step 3b": nesting mold tubes on the inner and outer walls of the stent, then heating in a vacuum oven at 60° C.~80° C. for 30 minutes~2 hours until the first bioabsorbable polymeric material is combined with the second bioabsorbable polymeric material.

14. The method for preparing an absorbable endoluminal stent according to claim 13, wherein in step 3b", after nesting the mold tubes on the inner and outer walls of the stent body, the method further comprises heating in the vacuum oven at 65° C.~76° C. for 40 minutes~100 minutes until the first bioabsorbable polymeric material is combined with the second bioabsorbable polymeric material.

15. The method for preparing an absorbable endoluminal stent according to claim 10, wherein, in the step 2, the through holes are further formed by chemical etching or physical punching.

* * * * *